US00PP22106P2

(12) United States Plant Patent
Dupont, Sr.

(10) Patent No.: US PP22,106 P2
(45) Date of Patent: Sep. 6, 2011

(54) ***HIBISCUS* PLANT NAMED 'DUP-CDS'**

(50) Latin Name: *Hibiscus rosa-sinensis*
Varietal Denomination: DUP-CDS

(76) Inventor: Robert J. Dupont, Sr., Plaquemine, LA (US)

( * ) Notice: Subject to any disclaimer, the term of this patent is extended or adjusted under 35 U.S.C. 154(b) by 0 days.

(21) Appl. No.: 12/800,679

(22) Filed: May 20, 2010

(51) Int. Cl.
*A01H 5/00* (2006.01)

(52) U.S. Cl. ..... Plt./157
(58) Field of Classification Search ..... Plt./257
See application file for complete search history.

*Primary Examiner* — Annette Para
(74) *Attorney, Agent, or Firm* — Robert S. Pippenger

(57) ABSTRACT

A new and distinct cultivar of *hibiscus* plant named 'DUP-CDS', characterized by glossy, dark green leaves, upright, moderately sturdy growth, and large flowers having a deep brown-orange pistil and center zone shading into a bright orange which extends to the petal margin., the underlapping petal edge is highlighted in deep orange.

5 Drawing Sheets

Figure 1:
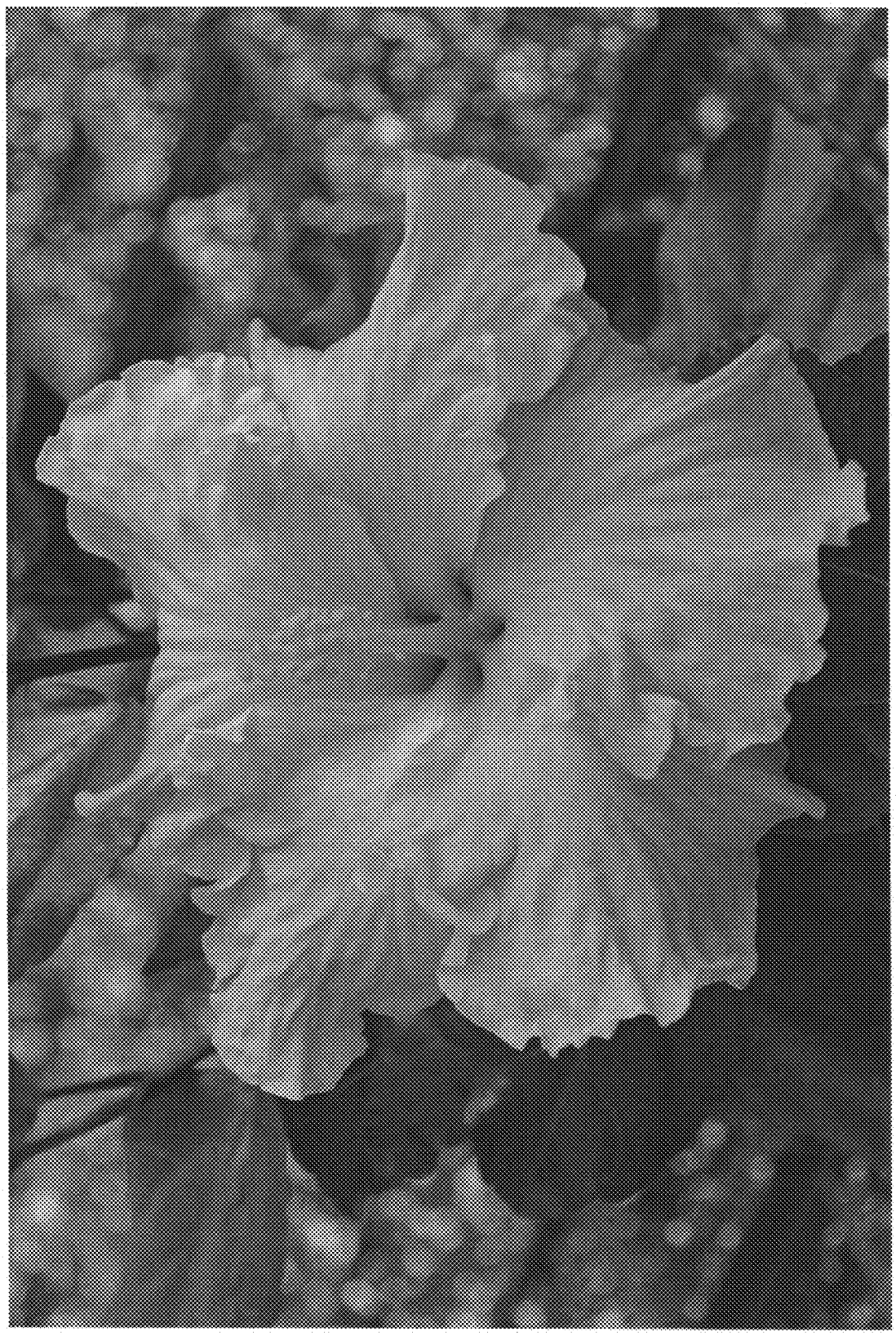

Latin name of the genus and species: *Hibiscus rosa-sinensis*.

Variety denomination: 'DUP-CDS'.

BACKGROUND OF THE INVENTION

The present invention relates to a new and distinct cultivar of *hibiscus*, botanically known as *Hibiscus rosa-sinensis* and hereinafter referred to by the cultivar name 'DUP-CDS.'

*Hibiscus* have been the subject of human admiration for centuries. While the ancestry of present *rosa-sinensis* hybrids is not precisely known, today's hybrids are thought to be the products of interspecific crosses involving Hawaiian, Polynesian and Asian species, among others, some of which may no longer be found in the wild, if they are to be found at all. It is thought that the first *hibiscus* identified as a *rosa-sinensis* was a double red form of uncertain origin found in cultivation in China, India and Polynesia, to be later introduced to Hawaii from Polynesia. It is known to have been grown in Europe during the Victorian era. Eventually, it was introduced to the continental United States where it was cultivated outdoors in the Deep South as well as in regions having subtropical or Mediterranean climates (Florida and Southern California, respectively). Indoor cultivation took place in the temperate regions of the U.S. It is speculated that the original *rosa-sinensis* is actually a species hybrid, possibly naturally arising, involving two or more species. Regardless, present day hybrids are descended from the original double form, and are thought to include in their ancestry *Hibiscus liliiflorus, H. arnottianus, H. schizopetalus*, as well as other species, particularly those native to Hawaii.

Today, after decades of extensive hybridization, the moniker "*rosa-sinensis*" almost certainly denotes complex interspecific hybrids. Such hybrids are usually far removed from their species ancestors in form and color. Flowers characterized by spectacular size, color intensity and, in the last several decades, ringed and spotted patterns have been produced by U.S. hybridizers in Louisiana, Florida, Hawaii, Texas and elsewhere. Other hotbeds of *hibiscus*-breeding activity include Australia, and more recently, Tahiti. Today's flowers are removed from their species ancestors to such an extent that it is almost impossible to unravel the species component contributions which comprise a modern hybrid *hibiscus*.

However, in the past, despite the fact that hybridization was giving rise to flowers of spectacular size and color intensity, very few if any early hybrids attracted the attention of large scale commercial propagators. While the flowers were truly some of the most impressive in the entire plant world, hybridizers had been selecting predominantly for bloom characteristics. As a result, many of these spectacular hybrids were weak plants which, even with the best care, were short-lived and difficult to grow. The occasional production of a spectacular bloom was enough to keep the interest of those truly dedicated to growing something rare and special, and thus new hybrids continued to be produced by hobbyists with abundant passion and small amounts of greenhouse space. As a result, more breathtaking varieties were produced each year, to be distributed via grafting among dedicated hobbyists, only to die out within a time span of 10 or 15 years. It should be noted that the majority of the varieties introduced in the 1960's, 70's and even many from the 1980's and 90's are likely to be lost to cultivation, if they are not already.

Progress toward the development of a plant which an average gardener could easily grow and enjoy was slow to nonexistent. Many varieties were difficult to root from cuttings, and even if they did root, many varieties, when grown on their own roots, were extremely susceptible to fungal and bacterial root rots. Some grew acceptably only as grafted plants. However, grafted plants suffer from a serious disadvantage in that the quality of the graft generally determines the quality of the plant, making the production of uniformly vigorous plants a difficult task. Furthermore, after several years, it is common for grafted plants to develop stresses at the graft union due to the unequal growth rates of the rootstock and the scion. Such stresses can eventually lead to loss of vigor and death of the plant. Moreover, grafting does not completely cure the problem of root rot; surprisingly, the rootstock, when grafted to a root rot susceptible scion was generally still more likely to suffer rot than a plant of the rootstock variety. For example, a plant of 'Seminole Pink,' a garden variety commonly used as a rootstock, is highly resistant to root rot. However, when 'Seminole Pink' is used as a rootstock for 'Romeo,' a modern hybrid which is prone to root rot, the grafted plant, while less susceptible than Romeo, is more susceptible than a plant of Seminole Pink.

Perhaps the most detrimental disadvantage of grafted plants is the introduction of viruses into the scion from the rootstock. Rootstock varieties are almost invariably old garden varieties which, over the years, have become infected with multiple viruses. While the performance of such vigorous garden varieties may be largely unaffected by virus infection, the hybrid scion of a grafted plant has generally been significantly less vigorous than the garden variety rootstock, and virus infection from the rootstock resulted in a weak plant. The problem only increased with successive generations of grafting, resulting in a rapid general weakening of a given variety over time.

Because many hybrids are shy bloomers at best, the extra stresses due to virus infection, grafting, low disease resistance, and the like generally gave sparse flower production, as well as a high number of deformed blooms. Furthermore, ordinary stresses such as over/under watering and mite/insect pests resulted in a high perecentage of bud drop. The buds of large-flowered hybrids often take relatively long times to reach blooming stage, and it was not uncommon to wait with anticipation while a bud swelled day by day, only to be disappointed when the mature bud toppled from its pedicel on the day it was to open.

Moreover, because of hybridizer emphasis on the flower, the plant was often relatively slow growing and sparsely clothed in leaves. Such plants usually do not attract purchasers as they do not have the appearance of garden-worthy specimens.

It has been noted in the industry that a hybrid *hibiscus* seems to sell only when it is bearing a bloom. The practical effect of all of the above-mentioned issues on a retail outlet is as follows. A garden center will order a number of plants. Many of the plants will arrive either in bloom or up to several days away from blooming. The blooming plants will generally sell the first day. On several subsequent days, new blooms will open on the remaining plants, and some of them will sell as well. However, by the fourth or fifth day, the lack of perfect growing conditions begins to take is toll, and the plants begin to drop their most mature buds. From this point on, the plants essentially sit around until they are marked down or even until they decline to such a degree that they must be discarded.

Such characteristics left *hibiscus* with the reputation that, despite the mesmerizing beauty of the flowers, they were for collectors who had time to attend to the seemingly exacting requirements of the plants. As a result, while new varieties were produced by hobbyists yearly, propagation of modern hybrids on a commercial scale was generally rare. Common garden varieties ('Seminole Pink', 'Brilliant', 'President', 'Painted Lady', 'Butterfly', 'Lago', for example), which are easy to root, fast growing, and tolerant of a wide range of growing conditions were the only *hibiscus* widely available. The "exotics" were of little interest to commercial growers.

Many new varieties of *hibiscus* representing a vast improvement in *rosa-sinensis* hybrids, have been produced by an intense hybridizing program conducted by the Inventor at his commercial nursery in Plaquemine, La. The objective of the program has been to produce varieties of *hibiscus* which root easily under commercial rooting conditions, grow well on their own roots, maturing rapidly into well-leaved, salable plants under commercial greenhouse conditions. Further objectives are to produce *hibiscus* cultivars as aforementioned, having large flowers with unique and desirable flower characteristics, such as size, color intensity and pattern.

Asexual reproduction of the new *hibiscus* by hardwood, semi-hardwood, and terminal cuttings taken in a controlled environment in Plaquemine, La., has shown that the unique features of these new *hibiscus* are stable and reproduced true to type in successive generations.

SUMMARY OF THE INVENTION

The cultivar 'DUP-CDS' has not been observed under all possible environmental variables. The phenotype may vary somewhat with variations in environment such as temperature, light intensity, nutrient and water status without, however, any variation in genotype. For example, during cooler weather, flowers of many *hibiscus* cultivars may demonstrate an increased intensity in pink tones. Furthermore, as with many varieties of *hibiscus*, cooler weather can result in a decrease in flower diameter, and a corresponding reduction in size of sepals and pistil. Moreover, as indicated below, plant characteristics vary greatly with culture, with internode spacings often increasing in warmer weather and with higher soil fixed nitrogen content. Plants grown at higher temperatures also exhibit a faster rate of growth. In general the plant used in the following description was grown at temperatures which never dipped below 55 F. Because the Inventor's one gallon pot plants are grown for an average time of about 5.5 to 6 months prior to sale, and the 10 inch pot plants are grown for an average time of about 7 to 8 months prior to sale, it is difficult to provide a precise temperature profile required to give the average plant measurements described in the below description. The growing period can encompass several seasons, with seasonal fluctuations in high/low temperatures as well as photo period. It is expected that the daily high temperature ranged from about 70 F to about 95 F, and the daily low temperature, which never dipped below 55 F, ranged from about 65 F to about 80 F.

The following traits have been repeatedly observed and are determined to be the unique characteristics of 'DUP-CDS.' These characteristics in combination distinguish 'DUP-CDS' as a new and distinct cultivar.

1. Glossy, dark green leaves.
2. Upright, moderately sturdy appropriate for container production and culture.
3. Freely flowering habit.
4. A large flower characterized by a deep brown-orange pistil and center zone shading into a bright orange which extends to the petal margin. The underlapping petal edge is highlighted in deep orange.
5. The plant is at least as free-flowering as each parent, and has been found to root more easily under greenhouse conditions than either parent.

BRIEF DESCRIPTION OF THE PHOTOGRAPH(S)

The accompanying colored photographs illustrate the overall appearance of the new *hibiscus*, showing the colors as true as it is reasonably possible to obtain in colored reproductions of this type.

Colors in the photographs may differ slightly from the color values cited in the detailed botanical description which accurately describe the colors of the new *hibiscus*.

The photograph on the first sheet (FIG. 1) comprises a first day flower of 'DUP-CDS'.

Figure 2:
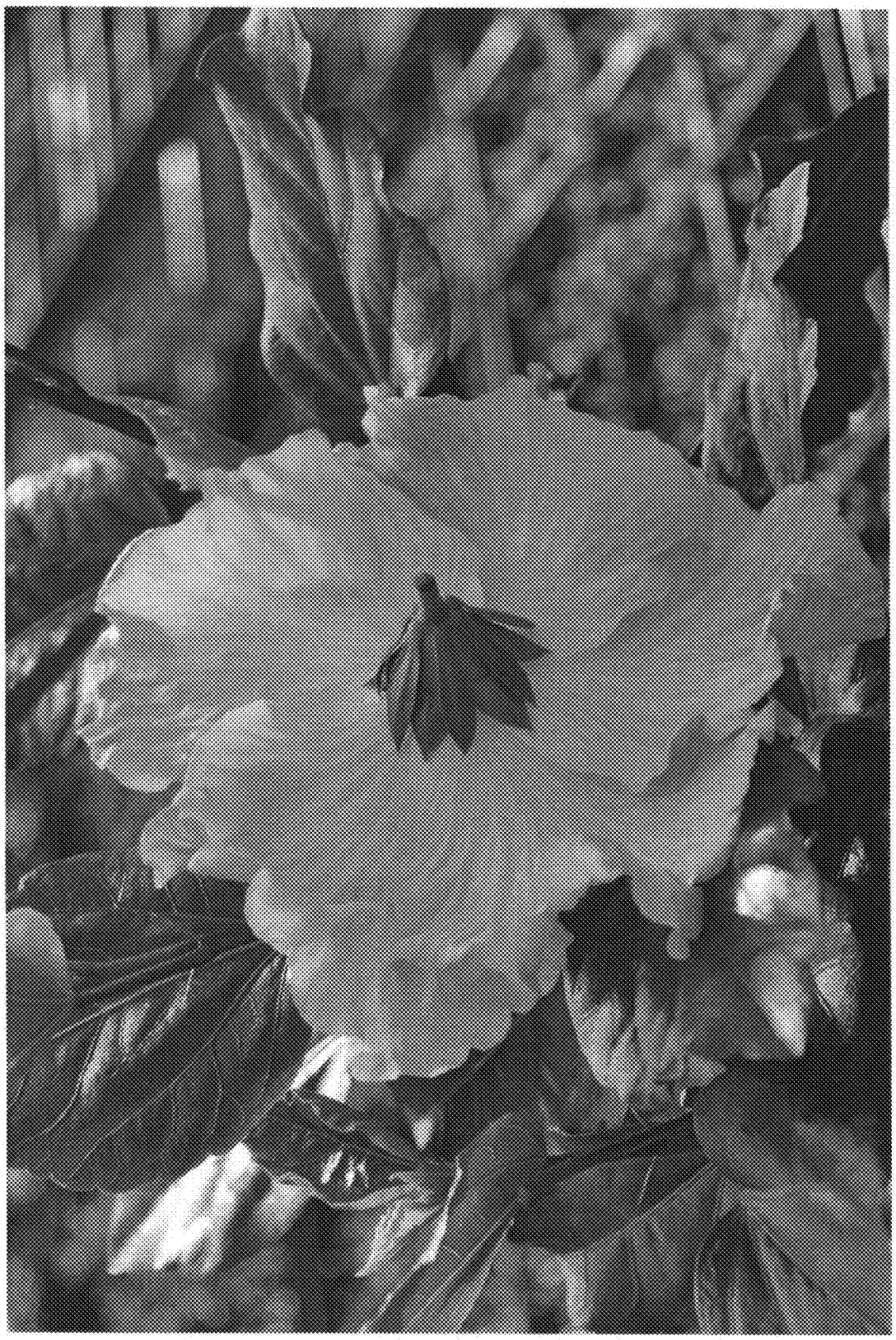

The photograph on the second sheet (FIG. 2) is a view of the reverse of the bloom.

Figure 3:
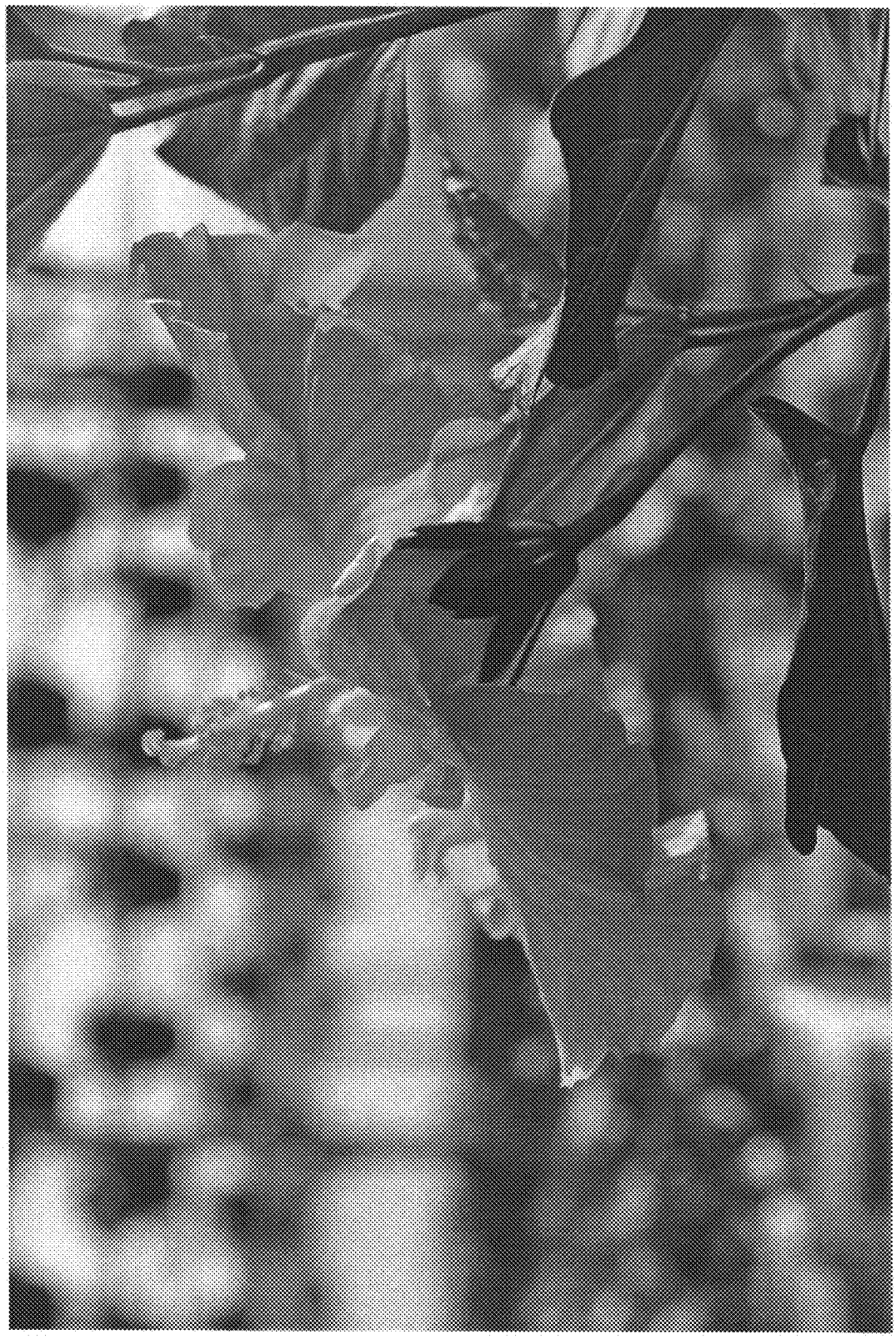

The photograph on the third sheet (FIG. 3) comprises a flower profile which demonstrates the relative proportions of the pistil and bloom diameter. The calyx is clearly visible.

Figure 4:
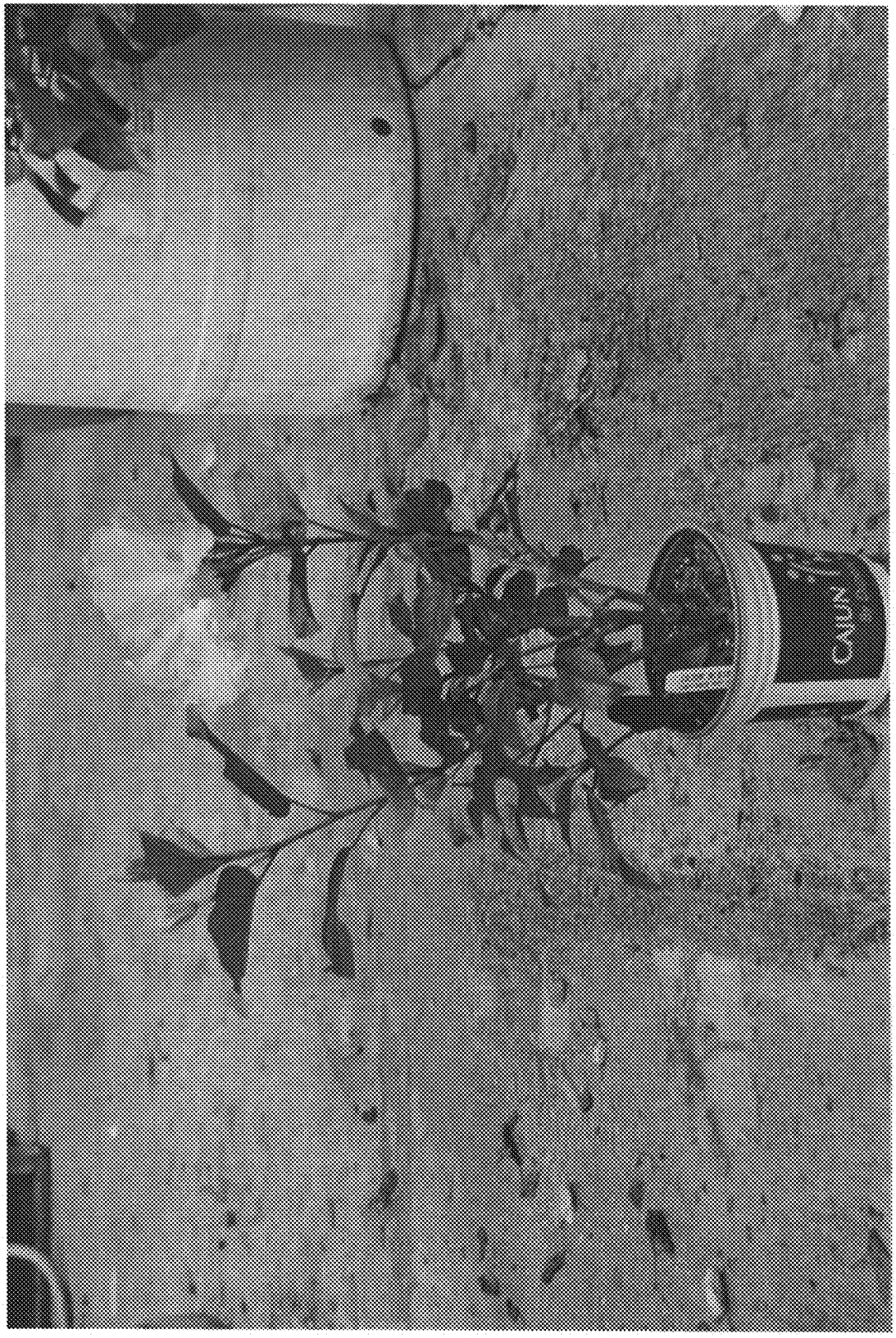

The photograph on the fourth sheet (FIG. 4) comprises one plant in a one gallon container.

Figure 5:
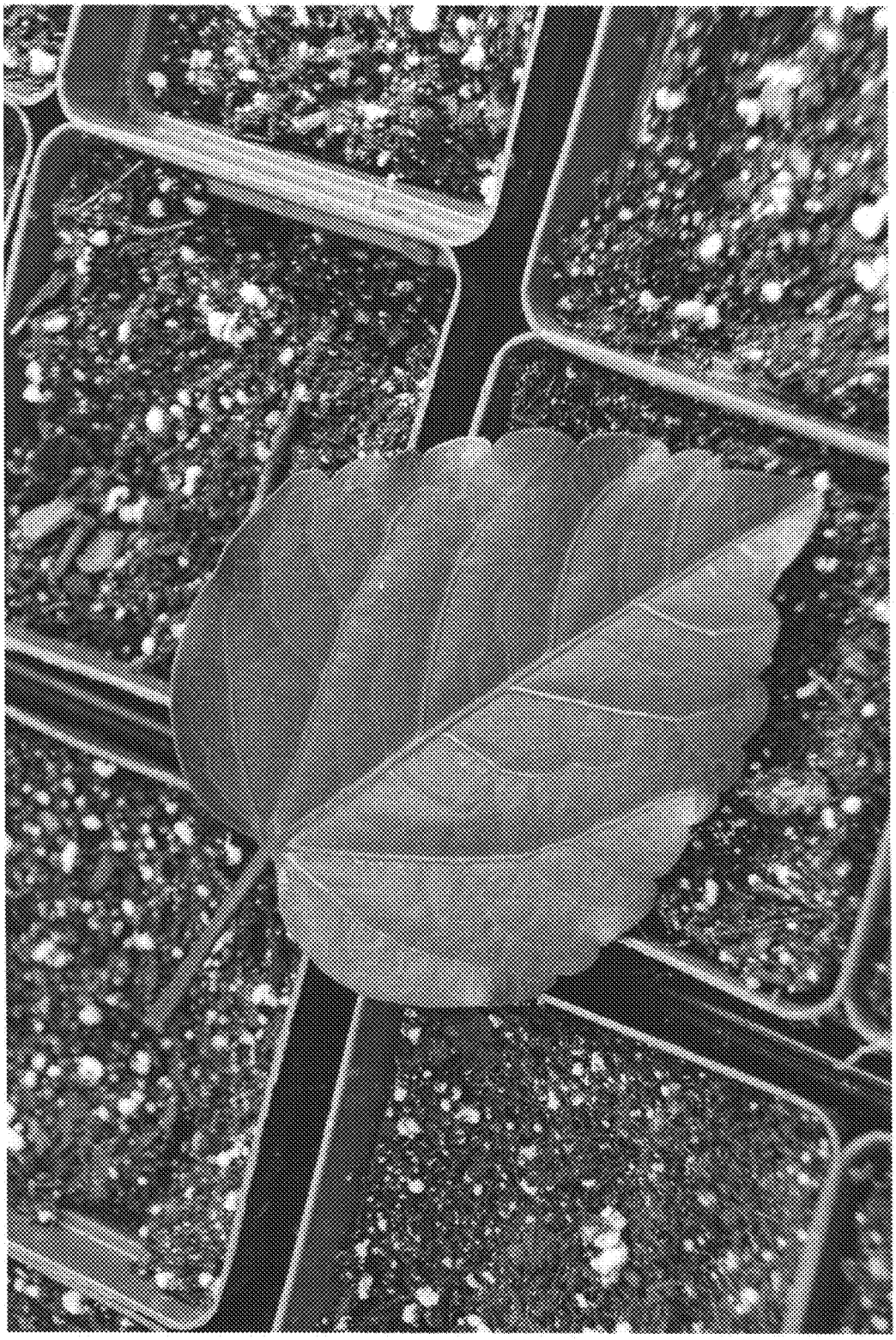

The photograph on the fifth sheet (FIG. 5) comprises a mature leaf.

DETAILED BOTANICAL DESCRIPTION

In the following description, color references are made to The Royal Horticultural Society Colour Chart except where general terms of ordinary dictionary significance are used. The following observations, measurements, and values describe plants grown in Plaquemine, La., with one plant per one gallon container. Plants used for the description were about 22 weeks old.

Botanical classification.—Hibiscus rosa-*sinensis*.

Parentage:

*Female or seed parent.*—Misfire (not patented).

*Male or pollen parent.*—Cherie (not patented).

Propagation:

*Type.*—'DUP-CDS' has been propagated by taking hardwood, semi-hardwood, and tip cuttings, with semi-hardwood preferred. It should be noted that many methods of asexual propagation, such as tissue culture and other cloning processes, can be expected to show some degree of success in the propagation of the present cultivar. However, of the methods tried by the Inventor, the use of semi-hardwood cutting has given the greatest yield of commercially salable plants. Asexual propagation has resulted in plants which have the flower and plant characteristics of the original 'DUP-CDS' plant, and thus the variety is stable. Cuttings from 'DUP-CDS' generally root well under commercial greenhouse conditions. While greenhouse conditions such as relative humidity and other factors such as cutting age prior to planting affect the take, it is not unusual to get a take of almost 100%. Please note that as successive generations of cuttings are raised, the raiser may experience a drop in take due to the incorporation of virus, particularly if at some point grafted plants are prepared, and cuttings are taken from such a plant.

*Time to initiate roots.*—An average time of initiation at approximately 22 C is approximately six weeks, with slightly longer times during winter at comparable temperatures, and slightly shorter times during summer at comparable temperatures.

*Time to develop roots.*—An average time, at approximately 22 C, of development of a root system after initiation, is approximately six weeks, with slightly longer times during winter at comparable temperatures, and slightly shorter times during summer at comparable temperatures. It should be noted that root initiation and development can be affected by greenhouse conditions, biological stressors such as disease organisms, as well as environmental stressors such as low or variant relative humidity, over- and under-watering, temperature variations or high or low constant temperatures. Thus, rooting times can be shorter or longer than the times given above depending on the values of many different characteristics during the rooting process known in the art.

*Root description.*—Fibrous and well-branched.

Plant description:

*Plant form and growth habits.*—Perennial evergreen having upright, moderately sturdy growth. The growth habit is generally compact. As recognized by one of skill in the art, internodal distance can be dependent upon greenhouse temperature/time profile, fertilizer availability profile, and other factors.

*Branching habit.*—Well-branched, developing approximately 4-5 laterals when a single stem plant is pinched back to a 5 inch height.

*Plant height, soil level to top of flowers.*—A salable plant in a one gallon nursery pot can be approximately 14 inches high and 8 inches wide. Please note that cultural variables such as those mentioned under "Plant form and growth habits," above, among others, can cause significant variation from the values given herein.

*Lateral branch description.*—The average branch characteristics of a salable plant grown in a one gallon nursery pot: Average Length: Approximately 8". Average Diameter: Approximately 0.4 cm measured at the transition from green to woody stem texture. Texture: Immature: Smooth. Mature: Woody and rough.

Mature foliage description:

*Arrangement.*—Alternate, single, numerous, symmetrical.

*Length.*—Approximately 9.8 cm.

*Width.*—Approximately 7.8 cm.

*Shape.*—Cordate to ovate.

*Apex.*—Acuminate.

*Margin.*—Crenate.

*Texture.*—Glabrous, rugose.

*Color.*—Young foliage, upper surface: More green than 147A; glossy. Mature foliage, upper surface: Generally darker than 147A; glossy.

*Petiole.*—Average Length: 3.8 cm. Average Diameter: 0.3 cm. Texture: Fine pubescence on upper surface; lower surface, glabrous. It should be noted that as with other plant growth characteristics, foliage color and size can vary with nutrient availability, greenhouse temperature, day length, and other conditions of culture.

Flower description:

*Natural flowering season.*—Year round, with number and size reduction in extended periods of cold weather, such as daytime temperatures of less than 60 C. Extreme heat can slow growth and flower production.

*Flower arrangement.*—Flowers arranged singly at terminal leaf axils. Somewhat free-flowering, with usually one to two developing flower buds per lateral branch, flowers generally face upward or outward.

*Flower appearance.*—Large single bloom. Flowers are open for one to two days before senescence, which is often accompanied by partial or full petal closure. Flowers persistent.

*Flower diameter.*—'DUP-CDS' flowers are generally in the range of from about 6.5" to 8" when fully open, with largest flowers produced during warm weather (for example, day and night time temperatures above 73 F).

*Flower depth.*—Flower depth was measured to average approximately 3.0 cm. Flower depth was measured after removal of a petal and a sepal to expose the base of the pistil. The measurement was taken on a fully opened flower in the direction of the pistil, from the base of the ovaries to the maximum height of the flower petal. The depth was measured by using the point of recurvature of the petal whorl. It should be noted that the petal whorl of *hibiscus* blossoms can flatten out during the day, or increase or decrease in curvature or degree of petal reflex during the day, and thus variance from the foregoing value is possible.

*Flower bud* (*just before showing color*).—Rate of opening: 1-2 days. Rate of opening is generally faster in warmer weather. Flower bud dimensions were measured on a bud which was approximately one day from opening. Bud length was measured from the tip of the bud to the abscission zone where bud and peduncle meet. The average length of a bud which is one day from opening is approximately 6.8 cm. Bud diameter was measured at the widest part of the bud, an area approximately halfway up the outside of the developing petals. The average diameter of a bud which is one day from opening is approximately 3.0 cm. It should be noted that bud dimensions can vary somewhat with cultural conditions, and variations can even be observed in buds which are at the same stage of development. Shape: Roughly acuminate to ovate.

*Petals.*—Texture: Smooth, satiny, rugose. Arrangement: The corolla consists of five petals arranged in a whorl, having regular partial overlap, even when the flower is fully open. Shape of a petal: Roughly spatulate, with a rounded apex and a truncate base. The margin of each petal is undulate and entire, such that the margin of the flower appears to be undulate, and the overlap is excellent such that the flower margin appears circular. A representative petal length was measured to be 9.2 cm, and was taken from the base of the petal to the farthest point on the margin opposite the base. A representative width is 8.6 cm, and was measured perpendicularly to the pistil at the widest point of the petal. Petal size can vary with cultural conditions, such as temperature, and thus the flower size and shape can vary as well. Often, flowers which are produced at colder temperatures are smaller and appear more fully overlapped, giving almost a wheel-shaped appearance. When fully open, the edges of 'DUP-CDS' flowers can be somewhat recurved, but generally the presentation is such that the fully opened blooms are flat to somewhat ruffled. The color of a warm weather flower is described below. It has been observed that variations in temperature can effect the stronger or weaker expression of certain pigments, changing the balance of color, and thus variations in color intensity and pattern can occur with temperature. Cooler weather may increase the presence and/or intensity of pink or orange tones over the entire flower. It should be noted that the colors of *hibiscus* are among the most changeable of all flowers. A newly opening morning bloom generally has the most intense coloration, but as the flower flattens out and is exposed to the sun, many pigments begin to fade immediately, resulting in a flower which can look like a different variety altogether. While the flower of 'DUP-CDS' fades less than those of many other varieties, exposed to strong sun, the petals can fade such that they are mostly a uniform soft yellow by the end of the first day. The morning colors are described below. Color: Upper surface: 32B pistil and center zone shading into a 24B which extends to the petal margin. The underlapping petal edge is highlighted in 30A. Lower surface: Uniform 18B shading to 19A at the overlapping side of the petal.

*Sepals.*—Unlike the petals, sepals are relatively invariant in color. Their size can be affected by the same cultural conditions which affect flower size. They are generally smooth and elongated oblong with acute apices (pointed tips). They are fused at the long edges into a cupped calyx bearing at its brim the five pointed tips. When the petals of the flower spread open, the five pointed tips, which are flush with the backs of the opening petals, are forced into a radiating five point star-shaped configuration, which can be observed on the profile and reverse pictures. A representative width, which is measured perpendicularly to the long axis of the sepal at the position on the sepal at which the oblong edges transition from fused to unfused, is approximately 1 cm. A representative length, measured on the sepal from the free point to the fused point is approximately 3.1 cm. Color: Upper surface: Close to 146A. Lower surface: Close to 147A.

*Peduncle.*—Length: 4.8 cm. Angle: Approximately 35 degrees from branch. Strength: Strong, flexible. Texture: Smooth.

*Reproductive organs.*—Androecium: Stamen number: Approximately 100. Anther shape: Crescent. Anther color: 32B. Amount of pollen: Moderate. Pollen color: 21A. Gynoecium: Pistil number: 1. Pistil length (from base of ovaries to top of stigma): 7.3 cm. Style length (from base of ovaries to stigma branching point): 6.9. cm. Style diameter, at base: 1.1 cm. Style color: Base: 32B. Midsection: 32B. Apex: 32B. Stigma number: Usually 5. Stigma color: 30A.

It should be noted that the dimensions of a *hibiscus* blossom generally change not only during bud development, but also during opening, as well as during the life of the opened flower. For instance, upon opening, the petals generally gain in length. Furthermore, after opening, the pistil continues to grow in length while the anther filaments which hold the pollen sacs increase in length, the pollen sacs open and the stigmas separate, each at the tip of a branched style structure. Toward the end of the flower life, possibly due to a reduction in turgor pressure, the pistil may shrink in length and the petals may slightly decrease in area. Usually, the senescing petals of the flower fold toward the pistil to some degree, in some cases, completely enfolding it.

Disease resistance: 'DUP-CDS' has not been observed to be resistant to pathogens common in *hibiscus*. However, it has been observed in the green house to have a higher resistance to root rot than that of many existing hybrid varieties grown on their own roots.

If desired, and if the risk of virus infection is of no concern, the present variety can be grafted onto a rootstock and be grown as a grafted plant.

It is claimed:

1. A new and distinct *hibiscus* plant named 'DUP-CDS', either grafted or on its own roots, as illustrated and described.

* * * * *